(12) United States Patent
Fujinuma et al.

(10) Patent No.: US 10,226,649 B2
(45) Date of Patent: Mar. 12, 2019

(54) HAIR DYEING OR BLEACHING METHOD

(75) Inventors: Hiroyuki Fujinuma, Tokyo (JP);
Kazuhiro Okada, Tokyo (JP);
Tomohito Koshika, Tokyo (JP);
Mitsuhiko Yamamoto, Tokyo (JP)

(73) Assignee: KAO CORPORATION, Tokyo (JP)

( * ) Notice: Subject to any disclaimer, the term of this patent is extended or adjusted under 35 U.S.C. 154(b) by 1226 days.

(21) Appl. No.: 12/532,934

(22) PCT Filed: Apr. 25, 2008

(86) PCT No.: PCT/JP2008/058125
§ 371 (c)(1),
(2), (4) Date: Sep. 24, 2009

(87) PCT Pub. No.: WO2008/136433
PCT Pub. Date: Nov. 13, 2008

(65) Prior Publication Data
US 2010/0126522 A1    May 27, 2010

(30) Foreign Application Priority Data

Apr. 27, 2007  (JP) .................................. 2007-120361

(51) Int. Cl.
*A45D 19/00*    (2006.01)
*A61Q 5/08*    (2006.01)
(Continued)

(52) U.S. Cl.
CPC ............. *A61Q 5/08* (2013.01); *A45D 19/02* (2013.01); *A61K 8/02* (2013.01); *A61K 8/19* (2013.01);
(Continued)

(58) Field of Classification Search
CPC .... A45D 19/02; A45D 2007/001; A45D 7/04; A45D 2019/0066
(Continued)

(56) References Cited

U.S. PATENT DOCUMENTS 3,341,418 A    9/1967    Moses et al.
3,709,437 A    1/1973    Wright
(Continued)

FOREIGN PATENT DOCUMENTS

DE    18 01 518    1/1971
DE    26 10 129 A1    10/1976
(Continued)

OTHER PUBLICATIONS

Translation of JP # 07-215352 to Kao Corp.*
(Continued)

*Primary Examiner* — Tatiana Nobrega
*Assistant Examiner* — Brianne Kalach
(74) *Attorney, Agent, or Firm* — Foley & Lardner LLP (57) ABSTRACT

The present invention is a method for hair dyeing or bleaching by discharging in a foam from a squeeze container 6 a mixed solution of a first agent A1 and a second agent A2 of a two-part hair dye or bleach composition to apply on the hair. In the present invention, the squeeze container which includes a container body 4 and a squeeze foamer 5 is used as the squeeze container 6. At least one of the first agent A1 or the second agent A2 contains a foaming agent. The mixed solution of the first and second agents has a viscosity (25° C.) of from 1 mPa·s to 100 mPa·s. The first agent A1 and the second agent A2 are mixed in the container body 4 so as not to produce a foam. Squeezing is carried out with the squeeze container 6 stood upright so that the mixed solution A3 does not reach an air induct path 12 of the squeeze foamer 5. As a result, the mixed solution of the first and second agents of the two-part hair dye or bleach composition can be stably discharged in a fine foam using a squeeze container.

17 Claims, 6 Drawing Sheets

(51) Int. Cl.
*A45D 19/02* (2006.01)
*A61K 8/02* (2006.01)
*A61K 8/19* (2006.01)
*A61K 8/22* (2006.01)
*A61K 8/41* (2006.01)
*A61Q 5/10* (2006.01)
*B05B 11/04* (2006.01)
*B05B 7/00* (2006.01)

(52) U.S. Cl.
CPC ............... *A61K 8/22* (2013.01); *A61K 8/415* (2013.01); *A61Q 5/10* (2013.01); *B05B 11/043* (2013.01); *A45D 2019/0066* (2013.01); *A61K 2800/87* (2013.01); *A61K 2800/88* (2013.01); *B05B 7/0037* (2013.01)

(58) Field of Classification Search
USPC ..... 132/202–205, 208–210, 221; 8/405–406, 8/435, 524, 527; 424/70.6
See application file for complete search history.

(56) References Cited

U.S. PATENT DOCUMENTS

| | | | |
|---|---|---|---|
| 3,823,231 A * | 7/1974 | Bucaria | 424/62 |
| 4,147,306 A | 4/1979 | Bennett | |
| 4,509,661 A | 4/1985 | Sugizaki et al. | |
| 4,531,659 A | 7/1985 | Wright | |
| 4,615,467 A | 10/1986 | Grogan et al. | |
| 4,823,985 A | 4/1989 | Grollier et al. | |
| 4,961,925 A | 10/1990 | Tsujino et al. | |
| 5,064,103 A | 11/1991 | Bennett | |
| 5,143,518 A | 9/1992 | Madrange et al. | |
| 5,651,793 A | 7/1997 | Hoeffkes | |
| 5,848,730 A | 12/1998 | Kawase et al. | |
| 5,888,484 A * | 3/1999 | Schmitt et al. | 424/62 |
| 5,961,665 A * | 10/1999 | Fishman | 8/406 |
| 5,968,486 A | 10/1999 | Newell et al. | |
| 7,955,400 B2 | 6/2011 | Fujinuma et al. | |
| 2004/0079383 A1* | 4/2004 | Wayne et al. | 132/208 |
| 2004/0213752 A1* | 10/2004 | Fujinuma et al. | 424/70.1 |
| 2010/0236570 A1 | 9/2010 | Fujinuma et al. | |
| 2010/0316583 A1 | 12/2010 | Fujinuma et al. | |

FOREIGN PATENT DOCUMENTS

| | | |
|---|---|---|
| DE | 41 23 941 A1 | 1/1993 |
| EP | 0 113 418 | 7/1984 |
| EP | 0 503 507 | 9/1992 |
| EP | 1 055 425 | 11/2000 |
| EP | 0 877 653 | 10/2002 |
| EP | 1 291 006 | 12/2003 |
| EP | 1 470 812 A1 | 10/2004 |
| EP | 2 062 562 | 5/2009 |
| EP | 2 087 878 A1 | 8/2009 |
| GB | 1 125 528 | 8/1968 |
| GB | 1 478 607 A | 7/1977 |
| GB | 2 254 341 | 10/1992 |
| GB | 2 293 157 | 3/1996 |
| JP | 48-068750 | 9/1973 |
| JP | 49-050144 | 5/1974 |
| JP | 55-049308 | 4/1980 |
| JP | 58-030282 | 6/1983 |
| JP | 59-108710 | 6/1984 |
| JP | 60-20262 | 5/1985 |
| JP | 61-143412 | 7/1986 |
| JP | 62-242609 | 10/1987 |
| JP | 63-246313 | 10/1988 |
| JP | 04-099711 | 3/1992 |
| JP | 04-282307 | 10/1992 |
| JP | 04-293568 | 10/1992 |
| JP | 5-5175 | 7/1993 |
| JP | 06-107530 | 4/1994 |
| JP | 06-271435 | 9/1994 |
| JP | 07-023293 | 3/1995 |
| JP | 07 215352 | 8/1995 |
| JP | 07 215353 | 8/1995 |
| JP | 07-267834 | 10/1995 |
| JP | 07-330559 | 12/1995 |
| JP | 07-330560 | 12/1995 |
| JP | 08-040837 | 2/1996 |
| JP | 08-119838 | 5/1996 |
| JP | 08-119839 | 5/1996 |
| JP | 08-165235 | 6/1996 |
| JP | 08-199188 | 8/1996 |
| JP | 08-230959 | 9/1996 |
| JP | 08-231345 | 9/1996 |
| JP | 08-231346 | 9/1996 |
| JP | 08-259426 | 10/1996 |
| JP | 08-268848 | 10/1996 |
| JP | 08-283695 | 10/1996 |
| JP | 2579516 | 11/1996 |
| JP | 09-002923 | 1/1997 |
| JP | 09-002925 | 1/1997 |
| JP | 09-025223 | 1/1997 |
| JP | 09-040534 | 2/1997 |
| JP | 09-136818 | 5/1997 |
| JP | 09-143040 | 6/1997 |
| JP | 09-506130 | 6/1997 |
| JP | 09-227347 | 9/1997 |
| JP | 09-234112 | 9/1997 |
| JP | 09-255541 | 9/1997 |
| JP | 09-301835 | 11/1997 |
| JP | 10-000397 | 1/1998 |
| JP | 10-025230 | 1/1998 |
| JP | 10-167938 | 6/1998 |
| JP | 10-287534 | 10/1998 |
| JP | 10-324357 | 12/1998 |
| JP | 11-018836 | 1/1999 |
| JP | 11-018837 | 1/1999 |
| JP | 11-050089 | 2/1999 |
| JP | 11-124321 | 5/1999 |
| JP | 11-139945 | 5/1999 |
| JP | 11-199454 | 7/1999 |
| JP | 11-206454 | 8/1999 |
| JP | 11-246369 | 9/1999 |
| JP | 11-286421 | 10/1999 |
| JP | 11-349453 | 12/1999 |
| JP | 2000-128215 | 5/2000 |
| JP | 2000-191471 | 7/2000 |
| JP | 2000-297018 | 10/2000 |
| JP | 2000-297019 | 10/2000 |
| JP | 2001-010930 | 1/2001 |
| JP | 2001-19626 | 1/2001 |
| JP | 2001-039460 | 2/2001 |
| JP | 2001-097834 | 4/2001 |
| JP | 2001-172166 | 6/2001 |
| JP | 2001-278742 | 10/2001 |
| JP | 2001-288054 | 10/2001 |
| JP | 2001-327321 | 11/2001 |
| JP | 2002-020247 | 1/2002 |
| JP | 2002-097121 | 4/2002 |
| JP | 2002-154938 | 5/2002 |
| JP | 2002-193771 | 7/2002 |
| JP | 2002-220329 | 8/2002 |
| JP | 2002-226340 | 8/2002 |
| JP | 2002-226344 A | 8/2002 |
| JP | 2002-284655 | 10/2002 |
| JP | 2003-012479 | 1/2003 |
| JP | 2003-026554 | 1/2003 |
| JP | 2003-040747 | 2/2003 |
| JP | 2003-063936 | 3/2003 |
| JP | 2003-073240 | 3/2003 |
| JP | 2003-073241 | 3/2003 |
| JP | 2003-081791 A | 3/2003 |
| JP | 2003-095900 | 4/2003 |
| JP | 2004 339216 | 2/2004 |
| JP | 2004-282308 | 10/2004 |
| JP | 2006-124279 | 5/2006 |
| JP | 2006 124279 | 5/2006 |
| JP | 2007-120360 | 5/2007 |
| JP | 2007-120361 | 5/2007 |
| JP | 2007-291015 A1 | 11/2007 |

(56) References Cited

FOREIGN PATENT DOCUMENTS

| | | |
|---|---|---|
| JP | 2007-314523 A1 | 12/2007 |
| JP | 2010-006803 | 1/2010 |
| JP | 2010-006805 | 1/2010 |
| WO | WO-91/14759 | 10/1991 |
| WO | WO-95/16023 | 6/1995 |
| WO | WO-00/76468 A1 | 12/2000 |
| WO | WO-01/85105 | 11/2001 |
| WO | WO-01/85113 | 11/2001 |
| WO | WO 2008/136441 | 11/2008 |
| WO | WO2009/054027 A1 | 4/2009 |
| WO | WO2009/054028 A1 | 4/2009 |
| WO | WO2009/054029 A1 | 4/2009 |
| WO | WO2009/054148 A1 | 4/2009 |

OTHER PUBLICATIONS

U.S. Appl. No. 12/739,835, filed Apr. 26, 2010, Fujinuma, et al.
U.S. Appl. No. 12/739,091, filed Apr. 21, 2010, Fujinuma, et al.
U.S. Appl. No. 12/739,610, filed Apr. 23, 2010, Fujinuma, et al.
U.S. Appl. No. 12/739,471, filed Apr. 23, 2010, Miyabe, et al.
U.S. Appl. No. 12/739,631, filed Apr. 23, 2010, Miyabe.
U.S. Appl. No. 13/107,183, filed May 13, 2011, Fujinuma, et al.
U.S. Appl. No. 12/849,576, filed Aug. 3, 2010, US2010/0316583 A1, Fujinuma, et al.
U.S. Appl. No. 13/146,157, filed Jul. 25, 2011, Iijima, et al.
Communication of a Notice of Opposition issued Jul. 5, 2011, for European Patent Application No. 08 752 159.7, which was filed on Apr. 25, 2008, now Patent No. 2087878.
Saito, Hiroaki "Foamer Yoki No Tokucho To Saikin No Gijutsu Doko", Fragrance Journal, vol. 34, No. 7, pp. 54-59 (Jul. 15, 2006) (with full English language translation).
Saito, Hiroaki "Foamer Yoki No Tokucho To Saikin No Gijutsu Doko", Fragrance Journal, vol. 34, No. 7, pp. 54-59 (Jul. 15, 2006) (with English abstract).
Food & Packaging, "New Products Instruction", vol. 35, No. 10, pp. 588-593 (1994) (with English translation).
Food & Packaging, "New Products Instruction", vol. 34, No. 9, pp. 531-535 (1993) (with English translation).
U.S. Appl. No. 12/529,553, filed Sep. 2, 2009, Fujinuma, et al.
U.S. Appl. No. 10/829,954, filed Apr. 23, 2004, US2004/0213752 A1, Fujinuma, et al.
U.S. Appl. No. 12/995,378, filed Nov. 30, 2010, Ogawa, et al.
Official Communication with Observations of the opponent issued Mar. 23, 2012, in European Patent Application No. 08752159.7 which was filed Mar. 15, 2012 now Patent No. 2087878.
Notice of Opposition issued Apr. 2, 2012 in Europe Application No. 08752159.7 (With English Translation).
U.S. Appl. No. 13/308,017, filed Nov. 30, 2011, Fujinuma, et al.
"Make Your Hair Beautiful by Correct Usage—Hair Coloring ABC, revised edition." Feb. 2000. pp. 18-19. (with English translation).
371-EPO Response in European Patent Application No. 04009836. 0, dated Jul. 15, 2011.
Amendment filed Dec. 5, 2008 in European Patent application No. 0 400 9836.0.
Amendment filed Sep. 10, 2010 in Japanese application No. 2004-130373 (w/ English Translation).
Amendments to the Claims in Japanese Patent Application No. 2010-268209, filed on Apr. 8, 2011. (with English translation).
Analysis Methods for Surfactants, Research Workshop for Analysis of Surfactants, Oct. 1, 1975, pp. 117-118. (with English translation).
Analytical Chemistry Handbook, revised second edition, The Japan Society for Analytical Chemistry, Oct. 10, 1971, pp. 27-29. (with English translation).
Arai, Yasuhiro, "State-of-the-art: Hair Color Technology—Trends in development as seen in patents," Published by Fragrance Journal Ltd., Aug. 25, 2004, pp. 102-105, 212-213. (with English translation).

Chemical Daily, "Surfactant—Remarkable performance of nonionic surfactant (Market conditions in chemicals)," Jan. 25, 2002. (with English translation).
Chemical Daily, "Surfactant—Started growing responding to safety requirement," Jan. 19, 2000. (with English translation).
Chemical Daily. "Surfactant—Penetrated to the various fields taking advantage of unique characteristics." Jan. 21, 1999. (with English translation).
Close-up photocopy of the folding, collapsible box for "Poly Brillance Intensiv-Color-Crème" Aug. 25, 1997.
Communication Pursuant to Article 94(3) EPC dated Dec. 29, 2008 in European Patent application No. 0 400 9836.0.
Communication Pursuant to Article 94(3) EPC dated Jun. 28, 2010 in European Patent application No. 0 400 9836.0.
Communication Pursuant to Article 94(3) EPC dated Nov. 5, 2010 in European Patent application No. 0 400 9836.0.
Comprehensible Surfactant, first edition. Sep. 1, 2003. pp. 32-49. (with English translation).
Comprehensive Dictionary of Chemistry. Oct. 20, 1989. pp. 56, 60-61, 646-647, 1762-1763. (with English translation).
Office Action application filed in Japanese Application No. 2004-130373, dated Nov. 10, 2008.
Cosmetics Dictionary, first edition. Oct. 1, 1992. p. 373. (with English translation).
Cosmetics Handbook. Nov. 1, 1996. pp. 220-221, 441-444. (with English translation).
Decision of Refusal dated Jun. 16, 2010 in Japanese application No. 2004-130373 (w/ English Translation).
Decision to Refuse a European Patent Application dated Apr. 19, 2011, in regard to European Patent Application No. 08752171.2, filed Apr. 25, 2008.
Declaration by Akiko Nagabuchi (with English translation), served on Sep. 21, 2011, in regard to No. 22009, 2011 (yo).
Declaration by Hattori, Nobuhito, in regard to No. 22056, 2011 (yo), served on Dec. 28, 2011 (with English translation).
Denavarre, Maison G. The Chemistry and Manufacture of Cosmetics, second edition, vol. 4. 1975. pp. 841-863.
Dr. Matthias Schweinsberg, Test Report : Foaming Characteristics and Flow Characteristics of Cosmetic Products According to EP 1 291 006 AI, Feb. 17, 2012 with English Translation, served on Apr. 17, 2012 in regard to DE litigation No. 4a 028/11.
English translation of Amendment filed Mar. 9, 2009 in Japanese application No. 2004-130373.
English Translation of Decision to Grant a Patent dated Jan. 4, 2011 in Japanese Patent application No. 2004-130373 w/ Allowed Claims.
English Translation of Decision to Grant a Patent dated Jan. 4, 2011 in Japanese Patent application No. 2008-270377 w/ Allowed Claims.
English translation of Notification of Reasons for Refusal dated Jan. 6, 2009 in Japanese application No. 2004-130373.
English translation of Notification of Reasons for Refusal dated Jul. 22, 2008, in Japanese Application No. 2004-130373.
English translation of Remarks filed Mar. 9, 2009 in Japanese application No. 2004-130373.
English translation of Remarks filed Oct. 20, 2008 in Japanese application No. 2004-130373.
English translation of Submission of Publication and the like, dated Dec. 25, 2007, in Japanese Patent Application No. 2004-130373.
English translation of Submission of Publication and the like, dated Feb. 29, 2008, in Japanese Patent Application No. 2004-130373.
English translation of Submission of Publications and the like, filed Mar. 24, 2009, in Japanese Application No. 2004-130373.
English translation of Submission of Publications and the like, filed Nov. 10, 2008, in Japanese Application No. 2004-130373.
English translation of Submission of Publications and the like, filed Sep. 7, 2009, in Japanese Application No. 2004-130373.
Entire contents of the folding, collapsible box for "Poly Brillance Intensiv-Color-Crème" Aug. 25, 1997.
European Patent Office Communication dated Mar. 12, 2012 in European Patent Application 04 009 836.0.
European Patent Office Communication pursuant to Rule 114(2) EPC dated May 3, 2011, in European Application No. 04009836.0 filed Apr. 26, 2004.

(56) References Cited

OTHER PUBLICATIONS

European Search Report dated Aug. 23, 2004, in European Patent Application No. 04009836.0.
Excerpt from the Internet Website: www.bagonvalve.com in regard to Request Cancelation in Utility Model 20 2004 021 775, served on Apr. 18, 2012, (3 pp.).
Experiment Result Report 1 (with English translation), prepared on Jul. 11, 2011, in regard to No. 22009, 2011 (yo).
Experiment Result Report 5 (with English translation), served on Sep. 21, 2011, in regard to No. 22009, 2011 (yo).
Experimental Report 1 (with English translation), served on May 24, 2011, in regard to Heisei 23 year (Yo) No. 22009.
Experimental Report 2 (with English translation), served on May 25, 2011, in regard to Heisei 23 year (Yo) No. 22009.
Experimental Report 3 (with English translation), served on May 25, 2011, in regard to Heisei 23 year (Yo) No. 22009.
Experimental Result Report 13 (with English translation), served on Jan. 30, 2012, in regard to No. 22009, 2011 (yo).
Experimental Result Report 2 (with English translation), prepared on Jul. 22, 2011, in regard to No. 22009, 2011 (yo).
Experimental Result Report 6 (with English translation), served on Sep. 21, 2011, in regard to No. 22009, 2011 (yo).
Experimental Result Report 7 (with English translation), served on Sep. 21, 2011, in regard to No. 22009, 2011 (yo).
Experimental Result Report 8 (with English translation), served on Nov. 29, 2011, in regard to No. 22009, 2011 (yo).
Extended European Search Report dated Apr. 7, 2011, in European Application No. 10183376.2.
Extended European Search Report dated Nov. 4, 2010 in European Patent Application No. 10172766.7.
Feminine Treatment Hair Color 84, Certification for Approval for Manufacture of Quasi-Drug (with English Translation), Jan. 30, 1997.
Food and Packaging. vol. 34, No. 8, "Can Technology Study Group." Aug. 1, 1993. 6 pages.
Fragrance Journal. vol. 19, No. 6. "Recent Progress of Hair Dyes and Problems in Research and Development." Jun. 1991, pp. 26-27. (with English translation).
Hair Mode. Aug. 1996. No. 437, p. 108. (with partial English translation).
Handbook—Raw Materials of Cosmetics and Drugs—revised edition, Feb. 1, 1977, pp. 358-361. (with English translation).
Handbook "Poly Haarberater Coloration," original edition, 1992. pp. 76-77.
Henkel Study Report, Study No. 1100546-1, "Open Epicutaneous Test," served on Jan. 30, 2012, in regard to No. 22009, 2011 (yo).
Henkel Study Report, Study No. 1100546-2, "Single Application Epicutaneous Patch Test (24th Patch Test)," served on Jan. 30, 2012, in regard to No. 22009, 2011 (yo).
Henkel Study Report, "In Vitro Skin Irritation Test: Human Skin Model Test," served on Jan. 30, 2012, in regard to No. 22009, 2011 (yo).
Instructions for Feminine Retouch Color (with English Translation), Feminine Co., Ltd., published before Apr. 23, 2003. (served on May 25, 2011, in regard to Heisei 23 year (Yo) No. 22009).
Instructions for Feminine Treatment Hair Color (with English Translation), Feminine Co., Ltd., published before Apr. 23, 2003 (served on May 25, 2011 in regard to Heisei 23 year (Yo) No. 22009).
Instructions for use contained in the folding, collapsible box for "Poly Brillance Intensiv-Color-Crème" Aug. 25, 1997.
Ishikawa, Ryoji. Experimental Report, in regard to No. 22056, 2011 (yo). Dec. 28, 2011 (with English translation).
Iwakura, Ryouhei. "Present State and Problems of Hair Dyes." Fragrance Journal, Special Issue. No. 11, pp. 87-93. Dec. 25, 1990. (with English translation).
Japanese Collection of General Raw Materials for Cosmetics, fourth edition. Oct. 31, 1997. p. 583. (with English translation).
Japanese Patent Office Communication for application No. 2004-130373, dated Apr. 21, 2009, 3 pp. (includes statement submitted by third party).
Kishi, Haruo. Modern Fragrance and Cosmetics Science, 1st Edition. Mar. 20, 1979. pp. 42-47. (with English translation).
Mitsui, Takeo. New Cosmetic Science. Jan. 12, 1993. pp. 137-142. (with English translation).
Miyagi, Takashi. Food and Container, vol. 35, No. 10. pp. 588-593. 1994. (with English translation).
Miyagi, Takashi. Food and Container, vol. 35, No. 11. pp. 624-627. 1994. (with English translation).
Miyagi, Takashi. Food and Packaging, vol. 34, No. 8. "Does Non-Gas Container Cause a Boom? (Part 2)" 1993. pp. 467-471. (with English translation).
Miyagi, Takashi. Food and Packaging, vol. 34, No. 9. "Will Non-Gas Containers Create a Boom? (No. 3)" 1993. pp. 531-535. (with English translation).
Miyagi, Takashi. Food and Packaging, vol. 36, No. 3. Non-Gas Container Having Increased Level of Accomplishment (Part 3). 1995. pp. 154-158. (with English translation).
Miyagi, Takashi. Food and Packaging, vol. 42, No. 10. "Growing Pump Foamer Spreading into Western Markets, Part One: Mini-Foamer." Oct. 1, 2001. pp. 609-613. (with English translation).
Mottram, F.J., et al. Poucher's Perfumes, Cosmetics and Soaps, 10th ed. © 2000. "Hair Shampoos." pp. 295-301.
Murata, Seishiro. Cosmetic Dictionary, 1st edition. pp. 182-183, 666-667. Dec. 15, 2003. (with English translation).
Nakanishi, Fumio, et al. Science History of Hair Dye. Jan. 8, 1991. pp. 45-47. (with English translation).
Nakanishi, Fumio. Fragrance Journal. "Function of Recent Hair Coloring Agent and Developmental Trend Thereof." Aug. 15, 2001. pp. 39-45. (with English translation).
Nakanishi, Fumio. Fragrance Journal. "Future View of Hair Care Products." Jan. 15, 1997. pp. 49-56. (with English translation).
Nakanishi, Fumio. Fragrance Journal. "Recent Progress and Prospective Problems in Hair Colorants and Hair Lighteners" vol. 25, No. 1. Jan. 15, 1997. pp. 49-56. (with English translation).
New Cosmetic Science, second edition. Jan. 18, 2001. pp. 152-153. (with English translation).
Notification of Reason for Refusal, dated Jul. 22, 2008, in Japanese Patent Application No. 2004-130373.
Observations under Rule 114(2) EPC filed Apr. 9, 2010 in European Patent application No. 0 400 9836.0.
Office Action dated Nov. 5, 2010, in EP Application No. 04 009 836.0.
Omura, Takayuki, et al. Fragrance Journal. "Development Trend and Problems of Recent Hair Foam." Mar. 15, 1994. pp. 29-35. (with English translation).
Pharmaceutical Additive Dictionary, 2nd edition. pp. 153-154, 203-205. Mar. 25, 2002. (with English translation).
Photocopy of a folding, collapsible box for "Poly Brillance Intensiv-Color-Creme", dated as Aug. 25, 1997.
Prettia Product Information (with English Translation), Kao Corporation, published after Apr. 23, 2003. (served on May 25, 2011 in regard to Heisei 23 year (Yo) No. 22009).
Publication of Unexamined Patent Application JP 2003-81369, Mar. 19, 2003.
Quasi Drugs Manufacturing Material Specification 2006, first edition. pp. 527-528. Jun. 16, 2006. (with English translation).
Remarks filed Feb. 25, 2011 in European Patent application No. 08 752 171.2.
Reply to EESR in European Patent Application No. 10172766.7, Apr. 29, 2011.
Response to Communication filed Aug. 10, 2010 in European Patent application No. 0 400 9836.0.
Response to Communication filed Feb. 18, 2011 in European Patent application No. 0 400 9836.0.
Response to Communication filed Jul. 8, 2009 in European Patent application No. 0 400 9836.0.
Response to Communication Pursuant to Article 96(2) EPC filed Apr. 25, 2007 in European Patent application No. 0 400 9836.0.

(56) References Cited

OTHER PUBLICATIONS

Robbins, Clarence R. "Chemical and Physical Behavior of Human Hair, fourth edition." Jul. 10, 2006. pp. 221-231. (with English translation).
Rompps Chemie Lexikon, vol. 6, 8th Ed. 1998. p. 4531.
Sato, Takatoshi, et al. Fragrance and Cosmetics Science. "Permanent Hair Colorant." Sep. 20, 2001. pp. 138-140. (with English translation).
Sato, Takatoshi, et al. Fragrance and Cosmetics Science. Mar. 20, 1997. pp. 73-74. (with English translation).
Sato, Takatoshi. Science of Cosmetics. Mar. 20, 1997. pp. 138-140. (with English translation).
Shinbiyo Marcel. Oct. 1996. No. 31, pp. 73 and 83. Vivid Highlight advertisement page (with partial English translation).
Study Report, No. 1100547-1, "Dermatological Use Test with Hair-Coloring Products in Split Design," served on Jan. 30, 2012, in regard to No. 22009, 2011 (yo).
Submission of Publication and the like, dated Sep. 7, 2009, in Japanese Patent Application No. 2004-130373.
Submission of Publication issued Oct. 18, 2010, in JP Application No. 2004-130373 (with English translation).
Submission of Publications and the like, dated Mar. 24, 2009, in Japanese Patent Application No. 2004-130373. (with English translation).
Submission of Publications and the like, dated Nov. 10, 2008, in Japanese Patent Application No. 2004-130373.
Submission of Publications and the like, filed Apr. 8, 2009 in Japanese application No. 2004-130373 (w/ English Translation).
Submission of Publications and the like, filed Oct. 18, 2010 in Japanese application No. 2004-130373 (w/ English Translation).
Submission of Publications and the like, filed Oct. 25, 2010 in Japanese application No. 2008-270377 (w/ English Translation).
Tashima, Maseru, et al. Fragrance Journal. "Research and Development of Mist Foam Type Hair Styling Product." Dec. 15, 1992. pp. 61-69. (with English translation).
Taya-A.T. HM Education Mook., Series 3. "Knowing Mechanisms of Hair Coloring Agents." Apr. 10, 1998. pp. 8-9. (with English translation).
Test Report 4 (with English translation), served on Jul. 10, 2011, in regard to Heisei 23 year (Yo) No. 22009.
Test Report dated May 1, 2012, Hoyu Co., Ltd., Product Development Laboratory of General Research & Development Institute, Section Chief: Ryouji Ishikawa, served on May 11, 2012 in regard to No. 5260, 2012 (wa) with English translation, (13 pp.).
The Handbook of Oil Chemistry, 4th ed. "Lipids and Surfactants." Nov. 20, 2001. p. 522. (with English translation).
The Nikkan Kogyo Shimbun, Ltd. "Nonylphenol Identified as Endocrine Disrupting Chemical." Aug. 6, 2001. (with English translation).
Third Party Observation issued on May 3, 2011, in corresponding European Application No. 04 009 836.
Third-Party Observation filed on Apr. 27, 2011, in European Patent Application No. 0 400 9836.0 (including translation of submission).
Third-Party Observation filed on Dec. 19, 2009 in European Patent application No. 0 400 9836.0.
Third-Party Observation filed on May 10, 2010 in European Patent application No. 0 400 9836.0.
Third-Party Observation submitted Jun. 24, 2011, in European Patent Application No. 10172766.7.
Third-Party Observation submitted Jun. 24, 2011, in European Patent Application No. 10183376.2.
Third-Party Observation submitted Jun. 3, 2011, in European Patent Application No. 10172766.7, filed Apr. 26, 2004.
Third-Party Observation submitted May 12, 2011, in European Patent Application No. 04009836.0.
Third-Party Observation submitted May 3, 2011, in European Patent Application No. 0 400 9836.0.
Unichemy Corp. Experimental Report, in regard to No. 22056, 2011 (yo). Issued on Jun. 24, 2011 (with English translation).
Vivid Highlight. Iriya Cosmetics. Packaging and Instructions Insert. Sep. 6, 1996 (with English translation).
Watanabe, Yasushi, et al. Hair Science. "Hair Colorant." Feb. 1, 1986. pp. 144-150. (with English translation).
Written Argument filed by the Debtor (1/2) in the Case of Request for Provisional Disposition of Patent Right: No. 22056, 2011 (yo), served on Sep. 6, 2011. pp. 1-5, 29-34. (with partial English translation).
Written Demand for Appeal filed Sep. 10, 2010 in Japanese application No. 2004-130373 (w/ English Translation).
Yamagata, Yoshifumi, et al. Fragrance Journal. "Science of Foam: Function and Physical Properties of Foam." Dec. 15, 1992. pp. 37-47. (with English translation).
Yamakawa, Arata, et al. Fragrance Journal. "Development and Objective of Mousse Hair Cosmetic Products." Dec. 15, 1992. pp. 48-54. (with English translation).
Yasuda, Kosaku, et al. Knowledge of Fat and Oil Products. Aug. 25, 1977. pp. 240-244. (with English translation).
Japanese Office Action for related application No. 2008-115372, dated Sep. 4, 2012, with English translation.
Notification of Third Office Action Chinese Application No. 200780100733.0.dated Oct. 9, 2012.
Mitsui, Takeo; New Cosmetic Science—Second Edition; Jan. 18, 2001; pp. 470-475 (with English translation).
Declaration by Dr. Andrei Bureiko, dated May 18, 2015.
Experimental Report summarizing the results of a series of experiments conducted by Opponent 1.

\* cited by examiner

HAIR DYEING OR BLEACHING METHOD

TECHNICAL FIELD

The present invention relates to a hair dyeing or bleaching method using a two-part hair dye or bleach composition.

BACKGROUND ART

Two-part hair dye compositions or two-part hair bleach compositions which include a first agent containing an alkaline agent and a second agent containing hydrogen peroxide are widely used. Generally, such a two-part hair dye or bleach composition is an agent in the form of a gel or cream which has a post-mixing viscosity of about several thousand to several tens of thousand mPa's so that after applying on the hair the agent does not trickle down while being left.

To carry out hair dyeing or bleaching without any unevenness using a gel- or cream-formed two-part hair dye or bleach composition, first the first and second agents have to be vigorously shaken or mixed in a mixing container in order to carefully mix them. Furthermore, to carry out hair dyeing or bleaching without any unevenness using a gel- or cream-formed two-part hair dye or bleach composition, since the mixed solution has a high viscosity as mentioned above, not only skill is required, but the hair must be "pre-blocked" (in other words, the hair must be braided into sections at the front, sides, and rear of the head). Thus, required are a lot of time and effort to carry out such dyeing or bleaching.

On the other hand, two-part dye or bleach compositions are known which contain a surfactant in at least one of the first or second agents as a foaming agent so that the mixed solution of the first and second agents is discharged in a foam from a foamer container (Patent Documents 1 and 2). According to this two-part dye or bleach composition, by discharging the mixed solution of the first and second agents in a foam, the mixed solution can be simply applied on the hair without any unevenness. This allows a finish without any unevenness to be more easily obtained compared with when coating a gel- or cream-formed two-part hair dye or bleach composition.

Patent Document 1: JP-A-2004-339216
Patent Document 2: JP-A-2006-124279

DISCLOSURE OF THE INVENTION

Problems to be Solved by the Invention

In the case of using a squeeze container to discharge the mixed solution of the first and second agents of a two-part hair dye or bleach composition in a foam which is applied on the hair, the foam of the mixed solution has to be able to be easily spread over all of the hair. In addition, the foam quality also has to be formed with a fine texture to prevent drips from being formed after applying the foam of the mixed solution on the hair during the approximately 30 minutes that is usually required for them to be left. Furthermore, it is necessary to stably discharge the mixed solution in a foam from start to finish of its use.

In contrast, it is an object of the present invention to obtain a finish with dramatically less color unevenness when using a squeeze container to discharge a mixed solution of the first and second agents of a two-part hair dye or bleach composition in a foam by enabling fine foam to be stably discharged from start to finish.

Means for Solving the Problems

The present inventors discovered that when mixing the first and second agents of a two-part hair dye or bleach composition and discharging the resultant mixture in a foam from a squeeze container, by using a squeeze container equipped with a specific squeeze foamer, using first and second agents which produce a mixed solution with a viscosity in a specific range, and mixing the first and second agents so as not to produce a foam, the mixed solution which is subsequently discharged in a foam has greatly improved foam qualities, and can be stably discharged until the finish, thus enabling a finish with dramatically less color unevenness to be obtained. As a result of this discovery, the present inventors completed the present invention.

Specifically, the present invention provides a method for hair dyeing or bleaching using a two-part hair dye or bleach composition which is applied on hair containing discharging in a foam from a squeeze container a mixed solution of a first agent containing an alkaline agent and a second agent containing hydrogen peroxide, wherein the squeeze container is used which includes a container body and a squeeze foamer, the squeeze foamer having a gas-liquid mixing chamber for causing the mixed solution to foam by mixing air in the container body with the mixed solution, foam homogenizing means for homogenizing foam of the mixed solution which has been made to foam in the gas-liquid mixing chamber, and a discharge outlet for discharging the homogenized foam, at least one of the first or second agents contains a foaming agent, the mixed solution of the first and second agents has a viscosity (25° C.) of from 1 mPa·s to 100 mPa·s, mixing the first and second agents in the container body of the squeeze container so as not to produce a foam, and carrying out squeezing with the squeeze container stood upright so that the mixed solution does not reach an air induct path of the squeeze foamer.

Effect of the Invention

In the present invention, a specific squeeze container is used for the foamer container. In this squeeze container, fine foam cannot be discharged if the air induct path of the squeeze foamer is blocked by the mixed solution or the foam of the mixed solution during squeezing. However, if the mixed solution does not produce a foam in the container body, and, if the air induct path is not blocked by the mixed solution or foam of the mixed solution, fine foam can be discharged.

Furthermore, in the present invention, the mixed solution of the first and second agents of the two-part hair dye or bleach composition has a viscosity within a specific range. The first and second agents both have a viscosity which is considerably lower than the conventional gel or cream. Thus, the first and second agents can be homogenously mixed without having to vigorously shake the container in which they are filled, just by slowly switching the up/down positions of the container so that their mixed solution does not produce a foam.

Therefore, according to the present invention, by mixing the first and second agents so as not to produce a foam, and using the squeeze container while it is standing upright so that the mixed solution or the foam of the mixed solution do not reach the upper aperture of the container body so that the air induct path of the squeeze foamer is not covered by the mixed solution, fine foam can be stably discharged.

Thus, according to the method for hair dyeing or bleaching using a two-part hair dye or bleach composition of the present invention, a foamy mixed solution can be easily spread over all of the hair, enabling a finish without any color unevenness to be obtained. Furthermore, the problem of drips being formed while the foamy mixed solution is left after being applied on the hair can be resolved.

DESCRIPTION OF THE REFERENCE NUMERALS 1 two-part hair cosmetic for hair dyeing or bleaching
2 first container
3 second container
4 container body of second container or container body of squeeze container
5 squeeze foamer
6, 6B squeeze container
7 cap member
8 head member
10 mixing device
11 gas-liquid mixing chamber
12 air induct path
13 dip tube
14 foam homogenizing means
15 liquid path
16 liquid path
17 discharge outlet
18 foam homogenizing means
19 gap
20 check valve
A1 first agent
A2 second agent
A3 mixed solution

MODE FOR CARRYING OUT THE INVENTION

The present invention will now be described in more detail while referring to the drawings. It is noted that in the drawings, the same reference numerals represent the same or similar structural elements.

Figure 1A:
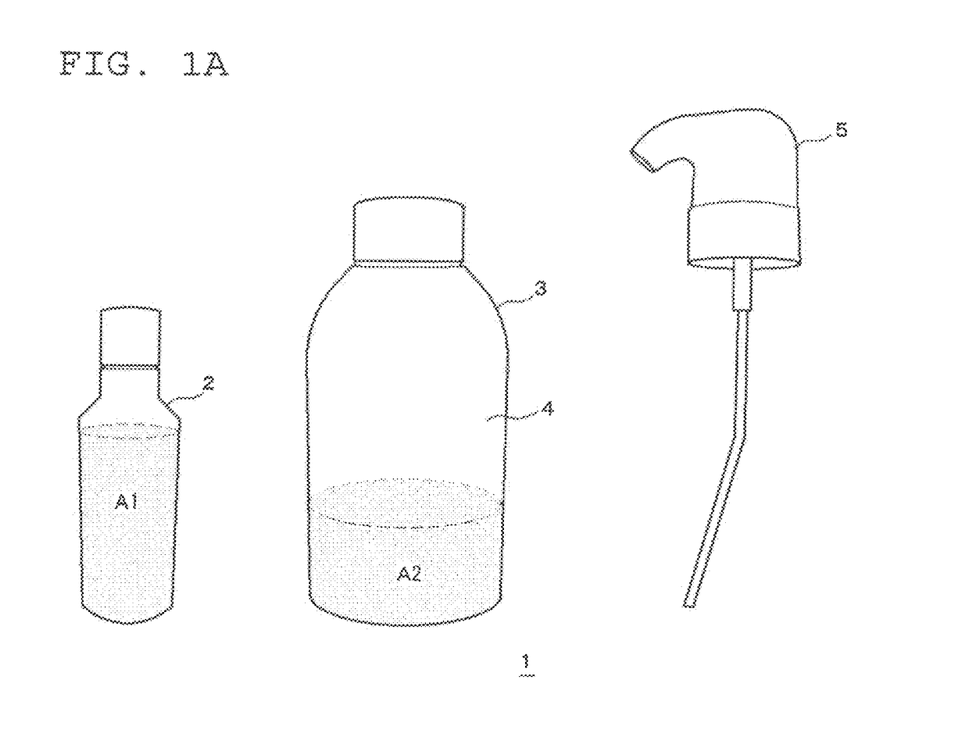
FIG. 1A is a schematic view of the two-part hair dye or bleach composition used in the present invention prior to the mixing of the first and second agents.
Figure 1B:
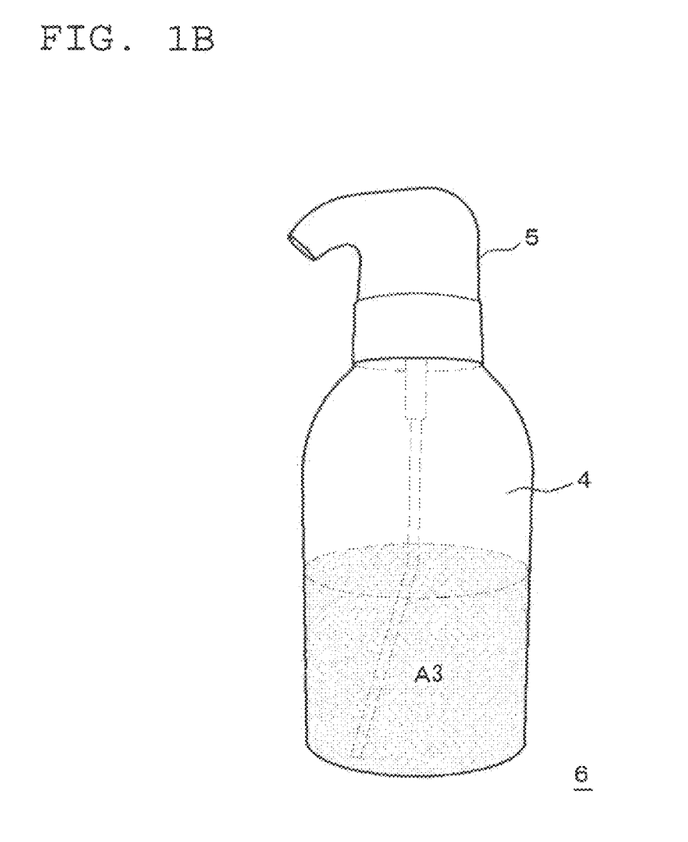
FIG. 1B is a schematic view of the two-part hair dye or bleach composition used in the present invention after the first and second agents have been mixed.

FIG. 1A is a schematic view of one embodiment of a two-part hair cosmetic 1 for hair dyeing or bleaching including the two-part hair dye or bleach composition used in the present invention and a squeeze container. FIG. 1A illustrates a pre-mixed state of the first and second agents. FIG. 1B illustrates a post-mixed state of the first and second agents of this two-part hair dye or bleach composition.

Figure 5:
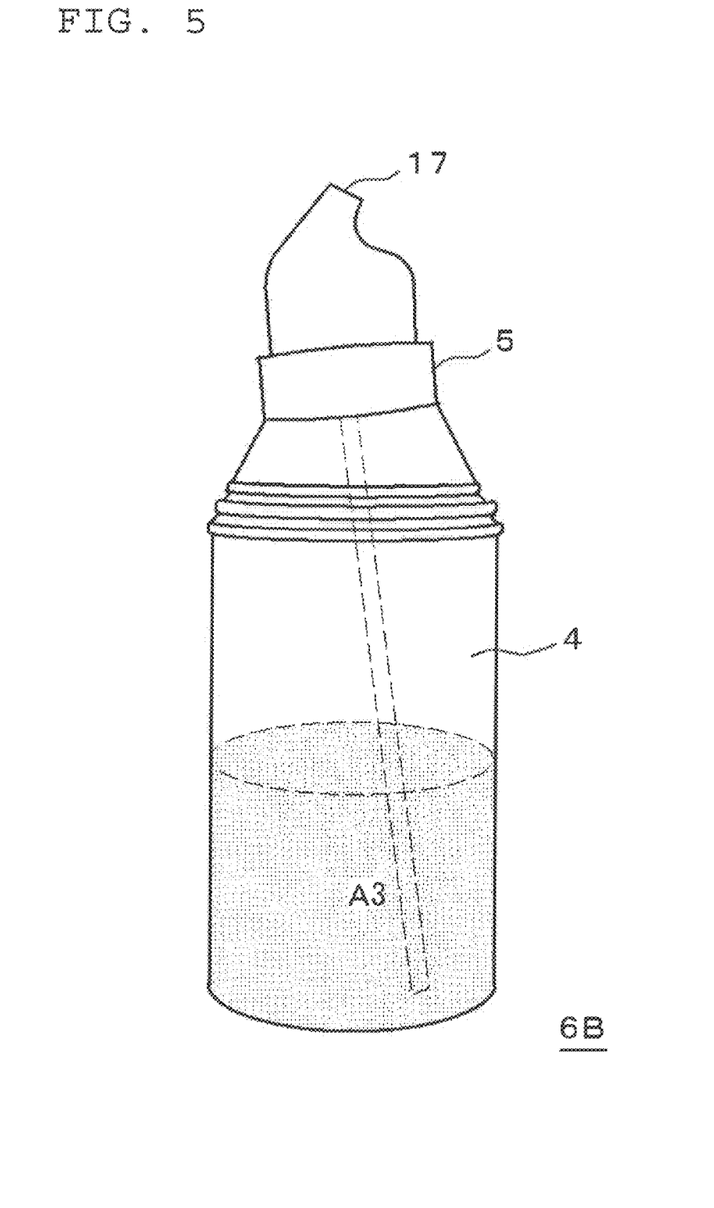
FIG. 5 is a schematic view of the squeeze container after the first and second agents have been mixed.

As illustrated in FIG. 1A, this two-part hair cosmetic 1 for hair dyeing or bleaching includes a first agent A1 filled in a first container 2, a second agent A2 filled in a second container 3, and a squeeze foamer 5. The container body 4 of the second container 3 also serves as the container body of the squeeze container. As illustrated in FIG. 1B, a squeeze container 6 is constituted of the container body 4 and the squeeze foamer 5. Here, the squeeze container is preferably such a container as causes a mixed solution to foam by mixing the mixed solution with air in the same container body. Examples of such a squeeze container include a container like the squeeze container 6 illustrated in FIG. 1B, which discharges its contents while in an upright manner (for example, "S1 Squeeze Foamer", manufactured by Daiwa Can Company). Further examples include a container such as the squeeze container 6B illustrated in FIG. 5, which is provided with a check valve (not shown) in the discharge path of the liquid so that it can discharge its contents either in an upright or inverted manner, since when the container is standing upright the portion which is the air induct path becomes the liquid induct path when inverted, while the dip tube which is the liquid induct path when the container is standing upright becomes the air induct path when inverted (for example, "Squeeze Foamer RF-270" manufactured by Toyo Seikan Kaisha, Ltd.). From the perspective of the discharge performance of the foam, a squeeze container which can discharge its contents in an upright manner as illustrated in FIG. 1B is preferred.

The concept of the "two-part hair dye or bleach composition" in the present invention includes hair dye or bleach compositions which contain a first agent and a second agent and which are used by mixing these agents at the time of use. In the case of a hair dye composition, the first agent A1 contains an alkaline agent and a dye, and the second agent A2 contains hydrogen peroxide. Furthermore, in the case of a hair bleach composition, the first agent A1 contains an alkaline agent but not a dye, and the second agent A2 contains hydrogen peroxide. In addition, this concept also includes embodiments wherein a third agent containing a persulfate is used. In such a case, the first, second, and third agents are used by mixing together.

Here, as the alkaline agent contained in the first agent A1, ammonia, an alkanolamine such as monoethanolamine, sodium hydroxide, and potassium hydroxide can be used. Furthermore, a buffer may be appropriately added, for example, an ammonium salt such as ammonium hydrogencarbonate and ammonium chloride, and a carbonate such as potassium carbonate and sodium hydrogencarbonate.

The concentration of the alkaline agent can be appropriately set so that the pH in the mixed solution A3 of the first agent A1 and the second agent A2 is from 8 to 12, and preferably from 9 to 11.

On the other hand, the concentration of the hydrogen peroxide in the second agent A2 is preferably in the range of from 1 mass % to 9 mass %, and more preferably in the range of from 3 mass % to 6 mass %. The hydrogen peroxide concentration in the mixed solution of the first agent A1 and the second agent A2 is preferably in the range of from 1 mass % to 6 mass %, and more preferably in the range of from 2 mass % to 5 mass %. Furthermore, to suppress decomposition of the hydrogen peroxide, the pH of the second agent A2 is preferably in the range of from 2 to 6, and more preferably in the range of from 2.5 to 4.

Both the first agent A1 and the second agent A2 preferably have water as their main solvent.

At least one of the first agent A1 or the second agent A2 used in the present invention contains a foaming agent. This enables the mixed solution A3 of the first agent A1 and the second agent A2 to easily foam by discharging the mixed solution A3 from the squeeze container 6. Furthermore, the produced foam has a longer life. Although the foaming agent may be anything so long as it has foaming properties, a surfactant is preferable. Examples of the surfactant include nonionic surfactants, anionic surfactants, cationic surfactants, ampholytic surfactants, semipolar surfactants, and the like. Among these, the use of an anionic surfactant is preferred, and using together with an ampholytic surfactant as well is more preferred. Examples of the anionic surfactant include an alkylsulfate, polyoxyethylenealkylethersulfate and the like. Examples of the ampholytic surfactant which can be used include fatty acid amidopropyl betaine, alkyldimethylamine oxide, alkylcarboxymethyl hydroxyethyl imidazolinium betaine, alkyldimethylaminoacetic acid betaine and sulfobetaine.

Furthermore, generally, considering that the first agent A1 in many cases contains ammonia or a carbonate and has a high ionic strength, to solubilize the dye or to improve the sense of feel, the first agent A1 preferably contains a nonionic surfactant, such as a polyoxyethylenealkylether, an alkylpolyglucoside, and an alkylalkanolamide. Among these, an alkylpolyglucoside or polyoxyethylenealkylether are preferred. More specifically, preferred examples of the alkylpolyglucoside have 8 to 14 carbon atoms on the alkyl group and an average degree of condensation of the glucoside of 1 to 2. Furthermore, preferred examples of the polyoxyethylenealkylether have 10 to 18 carbon atoms on the alkyl group and an average degree of polymerization of the polyoxyethylene of 5 to 40.

Furthermore, the second agent A2 may also contain a nonionic surfactant, such as a polyoxyethylenealkylether, an alkylpolyglucoside, and an alkylalkanolamide, and a cationic surfactant, such as alkyltrimethylammonium chloride and dialkyldimethylammonium chloride in order to improve the sense of feel.

When the two-part hair dye or bleach composition is for hair dyeing, the dye contained in the first agent A1 may be an oxidation dye or a direct dye. Examples of the oxidation dye include: dye precursors, such as para-phenylenediamine, para-aminophenol, toluene-2,5-diamine, N,N-bis(2-hydroxyethyl)para-phenylenediamine, 2-(2-hydroxyethyl) para-phenylenediamine, 4-amino-3-methylphenol, 6-amino-3-methylphenol, ortho-aminophenol and 1-hydroxyethyl-4,5-diaminopyrazole; couplers, such as resorcin, 2-methylresorcin, meta-aminophenol, para-amino-ortho-cresol, 5-(2-hydroxyethylamino)-2-methylphenol, meta-phenylenediamine, 2,4-diaminophenoxyethanol, and 1-naphthol; and the like. Examples of the direct dye include para-nitro-ortho-phenylenediamine, para-nitro-meta-phenylenediamine, basic yellow 87, basic orange 31, basic red 12, basic red 51, basic blue 99, acid orange 7, and the like.

It is preferred that at least one of the first agent A1 or the second agent A2 contains a higher alcohol, since this improves the life of the foam of the mixed solution discharged from the squeeze container 6, and suppresses drips from forming when the foam collapses after being applied on the hair. The higher alcohol preferably has 14 to 24 carbon atoms. Examples thereof include myristyl alcohol, cetyl alcohol, stearyl alcohol, behenyl alcohol, isostearyl alcohol, oleyl alcohol, and the like. These can be used as a combination of two kinds or more. Furthermore, these can be contained, based on the whole composition for hair dyeing after the first and second agents have been mixed, in an amount of 0.01 mass % to 3 mass %, preferably 0.1 mass % to 2 mass %, more preferably 0.2 mass % to 1 mass % and even more preferably 0.3 mass % to 0.8 mass %.

In addition, the first agent A1 and the second agent A2 may contain various additives as required. For example, to prevent the scalp from being irritated by an irritant component, such as hydrogen peroxide, which becomes more concentrated due to moisture evaporation after the mixed solution A3 of the first agent A1 and the second agent A2 is applied on the hair, addition of a nonvolatile, hydrophilic solvent, such as a polyol or lower alkyl ether thereof thereto are preferred. Furthermore, to give a conditioning effect to the hair, an ampholytic or cationic polymer, or a silicone and the like are also preferably added. Also they may appropriately contain a perfume material, an ultraviolet ray absorbent, a metal sequestering agent such as edetic acid, an antiseptic, a germicide such as methyl paraoxybenzoate, a stabilizing agent such as dibutylhydroxytoluene, 1-hydroxyethane-1,1-diphosphonic acid and sulfuric acid oxyquinoline, an organic solvent such as ethanol, benzyl alcohol and benzyloxy ethanol, a water-soluble polymer compound such as and hydroxyethylcellulose, a moisturizer, and the like.

Furthermore, the viscosity (25° C.) of the first agent A1 is preferably in the range of from 1 mPa·s to 50 mPa·s, more preferably in the range of from 3 mPa·s to 40 mPa·s, and even more preferably in the range of from 5 mPa·s to 30 mPa·s. The viscosity (25° C.) of the second agent A2 is preferably in the range of from 1 mPa·s to 300 mPa·s, more preferably in the range of from 3 mPa·s to 200 mPa·s, and even more preferably in the range of from 5 mPa·s to 100 mPa·s. The viscosity (25° C.) of the mixed solution A3 of the first agent A1 and the second agent A2 is in the range of from 1 mPa·s to 100 mPa·s, preferably in the range of from 3 mPa·s to 50 mPa·s, and more preferably in the range of from 5 mPa·s to 30 mPa·s. It is noted that these viscosity values are found using a B-type rotary viscometer (Model TV-10) with the No. 1 rotor manufactured by Tokimec Inc., after rotating the rotor for 1 minute. Measurement is carried out at a rotation speed of 60 rpm when the measuring target has a viscosity of 100 mPa·s or less, 30 rpm when the measuring target has a viscosity of from 100 mPa·s to 200 mPa·s, and 12 rpm when the measuring target has a viscosity of 200 mPa·s to 500 mPa·s. The viscosities of the first agent, second agent and mixed solution are taken as the values measured in a 25° C. thermostat bath. Furthermore, in the case of the mixed solution, the value measured immediately after mixing is used, and any temperature change due to heat of reaction is ignored. By setting the viscosity of the mixed solution in the above range, the mixed solution can be homogenously mixed without producing a foam. Furthermore, homogenous foam can be obtained which are easily applied on the hair, react well with the hair, and which do not easily form drips after being applied on the hair.

Adjustment of the viscosities of the first agent A1, second agent A2 and their mixed solution A3 to within the above ranges can be carried out by adding a water-soluble solvent such as ethanol to the first agent A1 and the second agent A2, or by appropriately adjusting the kind or added amount of the above-described surfactant, polyol or higher alcohol.

Figure 2:
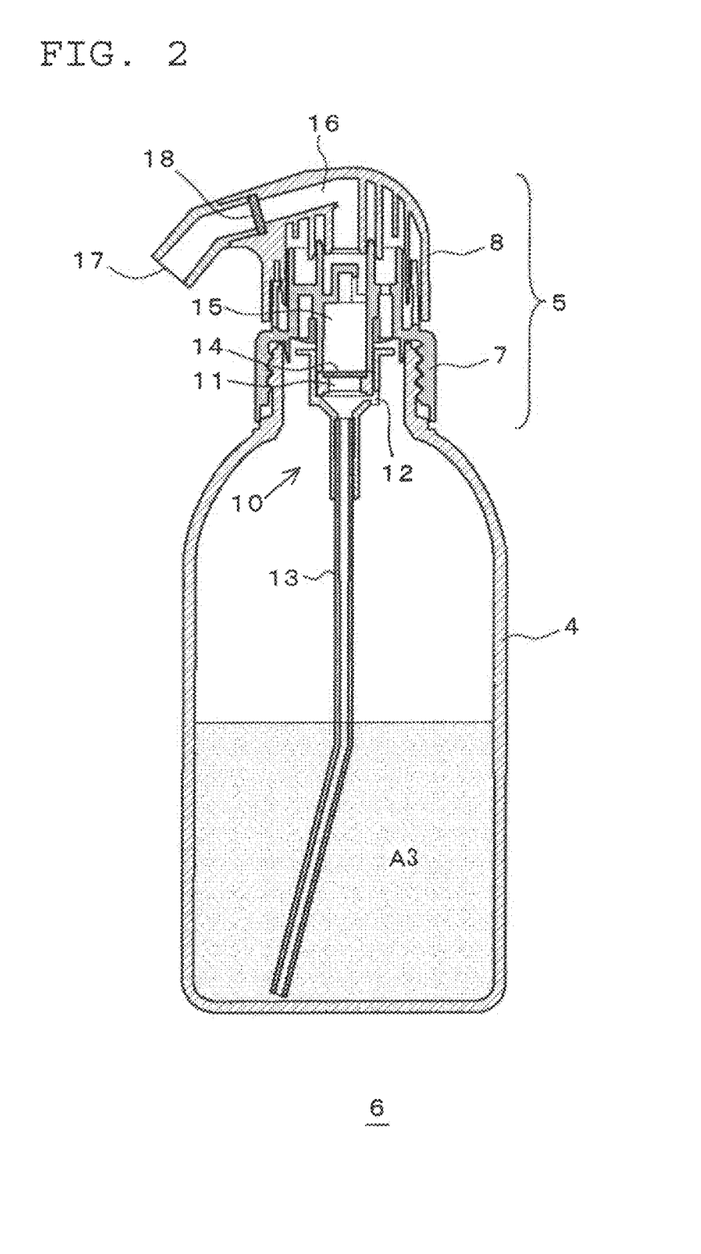
FIG. 2 is a cross-sectional view of a squeeze container.

Further, the squeeze container 6 for causing the two-part hair dye or bleach composition to foam has the same basic structure as a known squeeze container disclosed in, for example, JP-A-1995-215352. As illustrated in FIG. 2, the squeeze container 6 is composed of a flexible container body 4 and a squeeze foamer 5. The squeeze foamer 5 is composed of a cap member 7 attached to an aperture of the container body 4, and a head member 8 which sits over the cap member 7.

A mixing device 10 is fitted to the cap member 7 so as to hang down from the cap member 7. In the interior of the mixing device 10 are provided a gas-liquid mixing chamber 11, and an air induct path 12 through which the interior space in the container body 4 and the gas-liquid mixing chamber 11 are in communication with each other. Furthermore, in the mixing device 10, a dip tube 13 is fitted which extends into the container body 4. A net is attached to the ceiling of the gas-liquid mixing chamber 11 as foam homogenizing means 14, and the head member 8 side of the foam homogenizing means 14 serves as a liquid path 15.

On the other hand, on the head member 8 are provided a liquid path 16 connecting to the liquid path 15 of the cap member 7, and a discharge outlet 17 connecting to the liquid path 16. Furthermore, a net is provided in the liquid path 16 in the vicinity of the discharge outlet 17 as foam homogenizing means 18.

In the present invention, the foam homogenizing means 14 and 18 of the gas-liquid mixing chamber and the discharge outlet are not limited to a net. A porous material such as a sponge or a sintered body may also be used.

One method for using such a two-part hair dye or bleach composition is to, during use, first transfer the whole amount of the first agent A1 filled in the first container 2 to the container body 4 of the second container 3 filled with the second agent A2 to prepare the mixed solution A3. However, in the present invention this mixing is carried out so that the mixing of the first agent A1 and the second agent A2 produces as little foam as possible, or so that no foam are produced. Here, "not producing foam" or "no foam is produced" are a concept which excludes the intentional production of foam, but includes cases where a small amount of foam is unintentionally produced when the mixing is carried out like in the specific examples illustrated below. As long as a foam is not produced during the mixing, there are no restrictions on the mixing method. Examples of such methods include mixing carried out by shaking a test tube, or by moving the container body 4 from a roughly upright state to a state between an inverted state and a sideways state, and then once again returning to a roughly upright state. More specifically, the lid of the second container 3 is put on the container body 4 containing the first agent A1 and the second agent A2, and the cycle of moving the container body 4 from a roughly upright state to a state between an inverted state and a sideways state, and then once again returning to a roughly upright state, may be carried out 1 to 30 times, preferably 1.5 to 20 times, and more preferably 2 to 10 times, in 10 seconds. The operation of moving from a roughly upright state to a state between an inverted state and a sideways state, and then once again returning to a roughly upright state is carried out 1 to 15 times, preferably 2 to 10 times, and more preferably 3 to 7 times. A uniform mixed solution A3 can be easily obtained without a foam being produced even if the container body 4 is slowly shaken in this manner, since the first agent A1 and the second agent A2 used in the present invention have a much lower viscosity than a gel or cream type agent.

As illustrated in FIG. 1B, after the first agent A1 and the second agent A2 have been mixed, the squeeze foamer 5 is attached to the container body 4. It is noted that the mixing of the first agent A1 and the second agent A2 may also be carried out by transferring the whole amount of the first agent A1 to the container body 4 of the second container filled with the second agent A2, then attaching the squeeze foamer 5 to the container body 4 in place of the lid of the second container 3, and slowly shaking the container body 4 by a mixing method like that of shaking a test tube.

Then, the container body 4 is held in one hand and squeezed.

Figure 3:
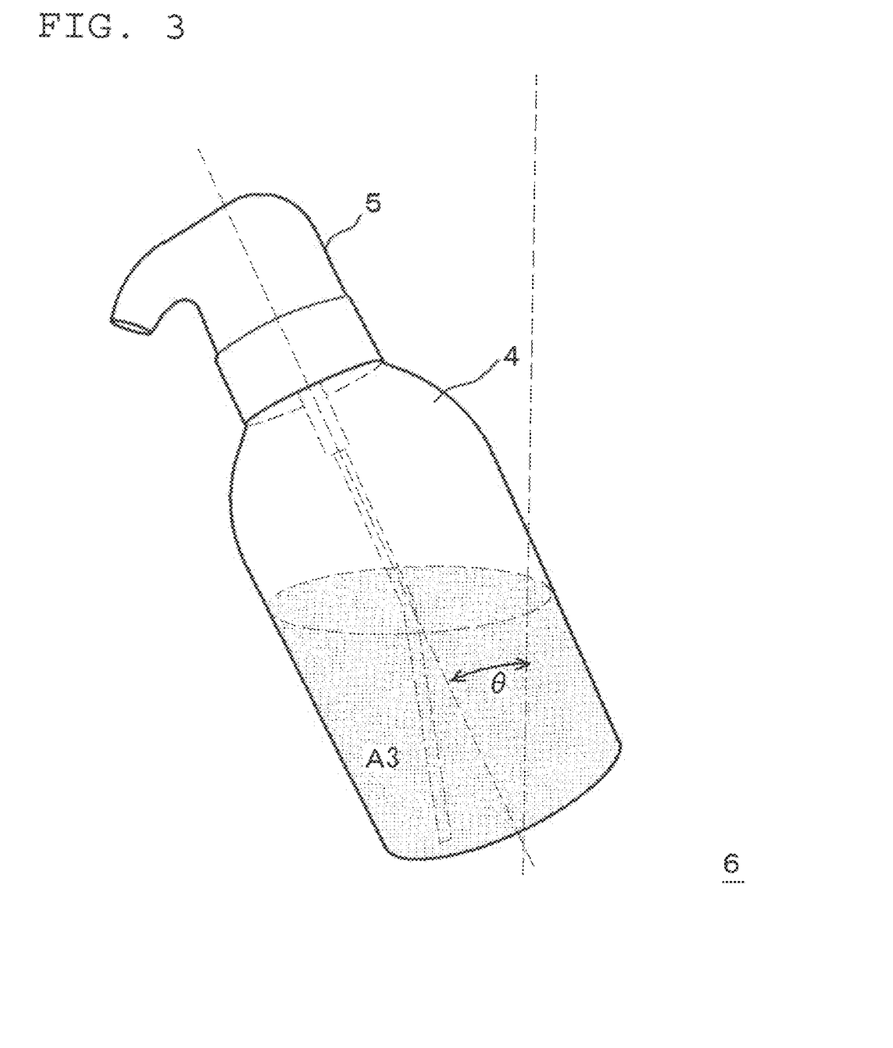
FIG. 3 is an explanatory diagram of the upright direction of the squeeze container.
Figure 4:
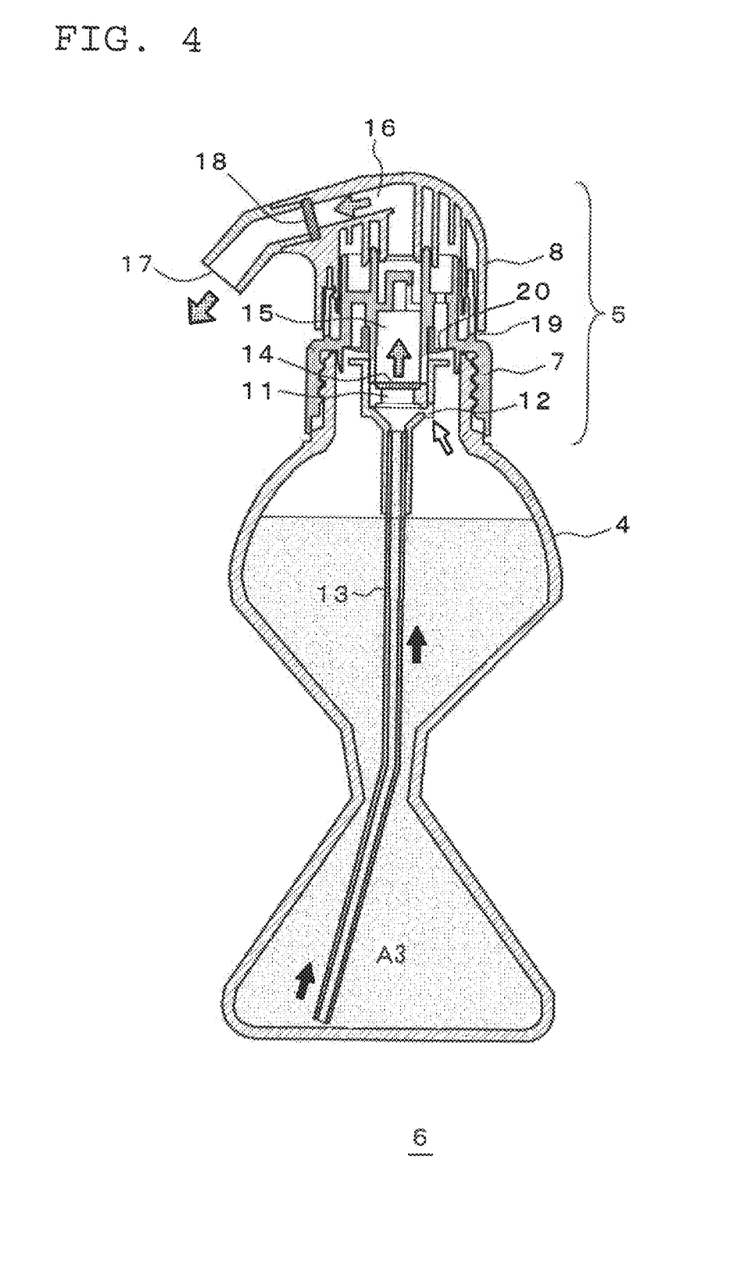
FIG. 4 is a cross-sectional view of the squeeze container when being squeezed.

During this squeezing, the container body 4 is squeezed while stood upright so that the mixed solution A3 or the foam of the mixed solution does not reach the upper aperture of the container body 4, specifically, so that the air induct path 12 is not blocked by the mixed solution A3 or the foam of the mixed solution. Although the upright direction of the container body 4 at this stage depends on the proportion of mixed solution A3 in the container body 4, as illustrated in FIG. 3, the direction may be set so that the angle θ formed with the vertical direction is in the range of from 0° to 60°, preferably in the range of from 5° to 50° and more preferably in the range of from 10° to 40°. As a result, as illustrated in FIG. 4, the mixed solution A3 in the container body 4 is pushed up in the direction of the arrow into the gas-liquid mixing chamber 11 via the tube 10. Since this also results in the air in the container body 4 being pushed into the gas-liquid mixing chamber 11 via the air induct path 12, in the gas-liquid mixing chamber 11, the mixed solution A3 foams, and the mixed solution A3 is discharged in a foam from the discharge outlet 17 via the two-stage foam homogenizing means 14 and 18.

Furthermore, it is preferred to squeeze this container body 4 slowly, so that the time required for one squeeze from the start of pushing the container body 4 until a fully pushed state is in the range of from 0.5 seconds to 5 seconds, preferably in the range of from 1 seconds to 4 seconds, and more preferably in the range of from 2 seconds to 3 seconds. As a result, the foam quality of the mixed solution A3 is stable.

Concerning the level of shape change of the container body 4 during squeezing, to increase the discharge amount of the mixed solution A3 from one squeeze, it is preferred to squeeze so that both opposing sides of the container body 4 touch each other. On the other hand, to squeeze with a suitably modified force in the vicinity of the middle in the height direction of the container body 4 with one's dominant hand, it is preferred to squeeze so to about ⅓ to ⅔ of the thickness in the minor axis direction.

Once the squeezing of the container body 4 is released, external air flows into the head member 8 from a gap 19 between the cap member 7 and the head member 8. Since this air enters the container body 4 via a check valve 20, the container body 4 is restored to its shape prior to squeezing, thereby allowing repeated squeezing. Thus, by repeating the squeezing 1 to 3 times, a lemon-sized amount of foam of the mixed solution A3 easy to handle in one hand can be discharged.

The discharged foam of the mixed solution A3 is collected in the palm of a gloved hand and are, for example, rubbed into the hair as upon using shampoo. It is also preferred to apply the foam to the hair so that the foam is further foamed. When applying the foam to all the hair, it is preferable to cover all the hair with the foam. From the perspective of preventing un-dyed portions, it is preferable to apply a larger amount of the foam of the mixed solution A3 on the hairline or parted areas than other areas. Furthermore, from the perspective of preventing drips and un-dyed portions, it is preferable to rub the hairline or parted areas in a circular motion.

In this case, the blocking operation which is conventionally, normally carried out by coating a hair dye composition is unnecessary. By rubbing the foam of the mixed solution A3 by hand, the foam can be spread from the roots to the tips of the hair in a short period of time. Therefore, color unevenness due to differences in time from after applying the foam of the mixed solution A3 on the hair until washing off is less likely to occur. In addition, since the foam of the mixed solution A3 is applied so as to foam further, drip formation caused by the applied foam collapsing can be suppressed.

Furthermore, since the foam can be spread on the hair in a short period of time, the foam of the mixed solution A3 can be applied from any part of the hair. This means that, as being different from in the case of using conventional liquid or cream two-part hair dye or bleach compositions, it is no longer necessary to apply such compositions from the neckline. The foam of the mixed solution A3 can be applied from a desired area. Usually, it is preferable to apply it from the hairline or parted areas.

After applying the foam of the mixed solution A3 on the hair in this manner, the hair can be subjected to hair dyeing or bleaching by leaving for a certain time, preferably 3 minutes to 60 minutes, and more preferably 5 minutes to 45 minutes, and then washed off.

EXAMPLES

The following examples were all carried out at room temperature (25° C.)

Example 1

The first and second agents of the two-part hair dyeing compositions having the blended compositions shown in Tables 1 and 2 were prepared. The viscosity and pH of each of the first and second agents were measured. Also measured were the viscosity and pH of mixed solutions in a 4:6 mass ratio of the first and second agents. Viscosity was measured using a B-type rotary viscometer with the No. 1 rotor by rotating at 30 rpm for 1 minute. The pH was measured using a pH meter (F-52, electrode 9611-10D, manufactured by Horiba, Ltd.). These results are shown in Tables 1 to 3.

On the other hand, the squeeze container 6 of FIG. 1B was constituted of a flexible container body 4 and a squeeze foamer ("S1 Squeeze Foamer" manufactured by Daiwa Can Company). This flexible container body 4 was made from polypropylene (PP), and had a resin weight of 17 g and an inner volume of 210 mL. The ⅔ power coefficient $\alpha$ calculated from this resin weight and inner volume ($\alpha = w/V^{2/3}$) was 0.46. The cross-sectional profile at a height 55 mm from the bottom, which corresponds to the middle in the height direction of the container body 4, was an ellipse (60 mm major axis, 44 mm minor axis, 21 cm$^2$ area). The ratio La/Lb of minor axis La to major axis Lb was 0.72.

The container body of this squeeze container was charged with 40 g of the first agent and 60 g of the second agent. Shaking was then carried out by moving the container body from a roughly upright state to an inverted state, and then once again returning to a roughly upright state at a rate of 3 times in 10 seconds. This shaking was carried out 5 times. As a result of this shaking, the mixed solution of the first and second agents was mixed without producing a foam. A squeeze foamer was then attached.

Next, the squeeze container was stood upright, and then squeezed for about 3 seconds per squeeze in the vicinity of the middle in the height direction of the container body 4 with a person's dominant hand to about ½ of the thickness in the minor axis direction to discharge foamy mixed solution. The foam quality was evaluated in the following manner for (a) gas/liquid mixed ratio, (b) foam life, and (c) drips.

Furthermore, foam discharged in the same manner was applied by rubbing on the hair of a wig (775s (model number) manufactured by Beaulax Co., Ltd. cut to a short hair style (3 cm below the chin)). This squeezing and application were repeated until the foam had been spread over all of the hair. The wig was then left for 30 minutes. At this stage, the coating time of from application start until the start of leaving the foam on the wig was measured (application method 1). Furthermore, separately to this, foam discharged in the same manner was applied by rubbing on the hair of the same type of wig, and foam was further foamed on the hair. This cycle of applying the foam and further foaming the foam applied was repeated so that the foam was spread over all of the hair. The wig was then left for 30 minutes. At this stage, the coating time of from application start until the start of leaving the foam on the wig was measured (application method 2). After being left for the time required, the foam was washed off, and then the wig was shampooed, rinsed and dried, in this order. The dried hair was evaluated for color unevenness in the following manner. It is noted that the applied amount for both application methods was 75 g.

These results are shown in Table 4.

(1) Foam Quality Evaluation Method (a) Gas-Liquid Mixing Ratio

To remove the top of the mixed solution in the squeeze container, 0.5 g was discharged. Then, 5 g was discharged into a 250 mL graduated cylinder. The gas-liquid mixing ratio (mL/g) was found by dividing the total volume (mL) of the foam and the liquid 1 minute after the initial discharge by 5 G. Using this value, the evaluation was carried out according to the following criteria.

"AA": 20 mL/g or more to less than 30 mL/g

"A": 15 mL/g or more to less than 20 mL/g, or 30 mL/g or more to less than 40 mL/g "B": 10 mL/g or more to less than 15 mL/g, or 40 mL/g or more to less than 50 mL/g "C": less than 10 mL/g, or 50 mL/g or more The evaluation criteria were determined from the perspectives of the amount placed on the hand, and the liquor ratio when coated on the hair.

(b) Foam Life

To remove the top of the mixed solution in the squeeze container, 0.5 g was discharged. Then, 5 g was discharged into a 250 mL graduated cylinder. The portion that had turned back into a liquid 5 minutes after the initial discharge was transferred to a graduated cylinder. This volume was measured and the foam life was evaluated according to the following criteria.

"AA": 0 mL or more to less than 0.6 mL

"A": 0.6 mL or more to less than 1.2 mL

"B": 1.2 mL or more to less than 1.8 mL

"C": 1.8 mL or more (c) Drips

Foam was applied on the hair according to the application method 1 or application method 2. Then, 30 minutes after the leaving was started, the state of drips was visually observed, and evaluated on a 3-point scale according to the following criteria.

"A": No drips formed

"B": A few drips formed (as a guide, the number of drips rolling down from the neckline to the skin)

"C": Drips formed (as a guide, liquid was trickling down from the hair tips)

(2) Color Unevenness Evaluation Method

Hair which had been subjected to a hair dyeing treatment was evaluated on a 5-point scale according to the following criteria from visual evaluations made by 5 specialist panelists. The average value was used as the evaluation result.
1: Color unevenness clear over a broad range of the hair surface
2: Color unevenness clear on part of the hair surface
3: Dyeing of the hair roots insufficient over all of the hair
4: Dyeing of the hair roots insufficient in part of the hair
5: Hardly any color unevenness over all of the hair

TABLE 1

| First agent blend component | Blend amount (mass %) |
|---|---|
| Meta-aminophenol | 0.03 |
| Toluene-2,5-diamine | 0.18 |
| Resorcin | 0.07 |
| 5-Amino-ortho-cresol | 0.04 |
| 2,4-Diaminophenoxyethanol hydrochloride | 0.06 |
| Strong ammonia water | 6.0 |
| Ammonium hydrogencarbonate | 10.5 |
| Decylpoly(1.4)glucoside | 6.16 |
| Polyoxyethylene(2) lauryl ether sodium sulfate | 2.7 |
| Polyoxyethylene(9) tridecyl ether | 0.5 |
| Polyoxyethylene(23) lauryl ether | 2.0 |
| Myristyl alcohol | 0.2 |
| Propylene glycol | 4.0 |
| Ethanol | 10.0 |
| Dimethyldiallylammonium chloride/acrylic acid copolymer | 0.4 |
| Dimethyldiallylammonium chloride/acrylamide copolymer | 0.5 |
| Royal jelly extract | 0.01 |
| L-arginine | 0.01 |
| Ascorbic acid | 0.4 |
| Sodium sulfite anhydride | 0.5 |
| Tetrasodium edetate dihydrate | 0.1 |
| Perfume | 0.95 |
| Purified water | Balance |
| Viscosity (mPa · s) | 14 |
| PH | 9.1 |

TABLE 2

| Second agent blend component | Blend amount (mass %) |
|---|---|
| Hydrogen peroxide water (35%) | 16.3 |
| Polyoxyethylene(2) lauryl ether sodium sulfate | 0.6 |
| Cetanol | 0.48 |
| Myristyl alcohol | 0.28 |
| Hydroxyquinoline sulfate | 0.04 |
| Hydroxyethane diphosphonic acid | 0.08 |
| Sodium hydroxide solution | (*1) |
| Purified water | Balance |
| Viscosity (mPa · s) | 15 |

(*1): the amount required for adjusting pH to 3.5

TABLE 3

| Mixed solution viscosity (mPa · s) | 7 |
|---|---|
| Mixed solution pH | 9.0 |

Example 2

Evaluation was carried out using a two-part hair dye composition in the same manner as in Example 1, except that the squeeze velocity per squeeze was 1.5 seconds. The results are shown in Table 4.

Example 3

Evaluation was carried out using a two-part hair dye composition in the same manner as in Example 1, except that the squeezing was performed by tilting so that the angle formed between the upright direction of the squeeze container and the vertical direction was a slope (θ=60°). The results are shown in Table 4. It is noted that even though the squeezing was performed by tilting to θ=60°, the mixed solution did not reach the air induct path of the squeeze foamer.

Comparative Example 1

Evaluation was carried out using a two-part hair dye composition in the same manner as in Example 1, except that a squeeze container (lacking a foamer and a dip tube) equipped with a tubular injection nozzle having a diameter which became narrower towards the tip was used instead of a squeeze container including a squeeze foamer, and that the mixed solution was directly discharged on the hair from the squeeze container. The results are shown in Table 4.

Comparative Example 2

Evaluation was carried out using a two-part hair dye composition in the same manner as in Example 1, except that when mixing the first and second agents, the mixed solution was made to produce a foam in the squeeze container by carrying out a shaking operation of moving the container body from a roughly upright state to a state between an inverted state and a sideways state, and then once again returning to a roughly upright state, thirty times at a speed of 4 times per second. The results are shown in Table 4.

Comparative Example 3

Evaluation was carried out using a two-part hair dye composition in the same manner as in Example 1, except that squeezing was performed by tilting the squeeze container (θ=75°) so that the mixed solution reached the upper aperture of the container body. The results are shown in Table 4.

TABLE 4

| | Example 1 | Example 2 | Example 3 | Comparative Example 1 | Comparative Example 2 | Comparative Example 3 |
|---|---|---|---|---|---|---|
| Foam state during mixing of the first and second agents (in the container) | A few foams could be seen on the surface of the mixed solution | A few foams could be seen on the surface of the mixed solution | A few foams could be seen on the surface of the mixed solution | A few foams could be seen on the surface of the mixed solution | A foam was produced as far as the upper aperture of the container body | A foam was produced as far as the upper aperture of the container body |

TABLE 4-continued

|  | Example 1 | Example 2 | Example 3 | Comparative Example 1 | Comparative Example 2 | Comparative Example 3 |
| --- | --- | --- | --- | --- | --- | --- |
| Squeeze speed per squueze (sec) | 3 | 1.5 | 3 | 3 | 3 | 3 |
| Standing state of the container during squeezing | Upright ($\theta = 0°$) | Upright ($\theta = 0°$) | $\theta = 60°$ | Inverted ($\theta = 180°$) | Upright ($\theta = 0°$) | $\theta = 75°$ |
| Foam quality evaluation (a and b are the average value of three times) |  |  |  |  |  |  |
| (a) Gas-liquid mixing ratio (mL/g) | AA 23 | A 15 | AA 22 | C 1 | C 3 | C 8 |
| (b) Foam life (mL) | AA 0 | AA 0.1 | AA 0 | C 5.0 | C 3.8 | B 1.3 |
| (c) Drips (application method 1) | A | B | A | C | C | C |
| (c) Drips (application method 2) | A | A | A | C | B | B |
| Coating time (min) (application method 1) | 8 | 8 | 8 | 15 | 8 | 8 |
| Coating time (min) (application method 2) | 10 | 10 | 10 | 20 | 10 | 10 |
| Hair color unevenness evaluation (application method 1) | 4.2 | 4.0 | 4.2 | 3.0 | 3.2 | 3.4 |
| Hair color unevenness evaluation (application method 2) | 4.8 | 4.8 | 4.8 | 3.6 | 4.0 | 4.0 |

From the results of Table 4, it can be seen that if, like in Examples 1 to 3, the first and second agents are mixed without producing a foam, and the mixed solution is applied on the hair by discharging in a foam, the gas-liquid mixing ratio is high, foam life is good, and drips are not formed. However, like in Comparative Example 1, if the foam is applied on the hair just in a liquid state without forming into a foam, drips are formed when a foam is produced on the hair.

Furthermore, like in Comparative Example 2, if a foam is produced when mixing the first and second agents, the foam quality of the mixed solution deteriorates, the gas-liquid mixing ratio is low, foam life is poor, and drips tend to form.

In addition, like in Comparative Example 3, if the squeeze container is tilted during squeezing so that the mixed solution reaches the upper aperture of the container body, the foam quality of the mixed solution deteriorates, the gas-liquid mixing ratio is low, foam life is poor, and drips tend to form.

Moreover, it can be seen that drips are less likely to form and color unevenness less likely to occur by further producing a foam on the hair so that the foam is spread over all of the hair.

INDUSTRIAL APPLICABILITY

The method for hair dyeing or bleaching using the two-part hair dye or bleach composition of the present invention enables more pleasant hair dyeing or bleaching.

The invention claimed is:

1. A method for hair dyeing or bleaching using a two-part hair dye or bleach composition which is applied on hair comprising:
    providing a solution comprising a first agent containing an alkaline agent and a second agent containing hydrogen peroxide in a container body of a squeeze container;
    mixing the solution to obtain a mixed solution by moving the container body in a cycle of moving the container body from a roughly upright state to a state between an inverted state and a sideways state, and then once again returning to a roughly upright state such that the mixing does not produce a foam in the container body of the squeeze container, and the mixing of the solution is carried out by moving the container body in the cycle 1 to 15 times at a speed of 1 to 20 times per 10 seconds;
    inserting a squeeze foamer at a top end of the container body of the squeeze container, the squeeze foamer comprising an air induct path, a gas-liquid mixing chamber, a foam homogenizing means and a discharge outlet;
    squeezing the squeeze container to mix air in the container body with the mixed solution in the gas-liquid mixing chamber of the squeeze foamer to cause the mixed solution to foam;
    discharging a foam of the mixed solution from the discharge outlet of the squeeze foamer via the foam homogenizing means, wherein
    at least one of the first or second agents contains a foaming agent, and the mixed solution has a viscosity (25° C.) of from 1 mPa·s to 100 mPa·s, and
    the mixed solution does not reach the air induct path of the squeeze foamer.

2. The method for hair dyeing or bleaching according to claim 1, wherein a time required for one squeeze is in a range of from 0.5 seconds to 5 seconds.

3. The method for hair dyeing or bleaching according to claim 1, wherein the squeeze container is squeezed to discharge the mixed solution when the squeeze container is disposed in an upright state.

4. The method for hair dyeing or bleaching according to claim 3, wherein the squeezing is carried out while an angle formed between an upright direction of the squeeze container and a vertical direction is in a range of from 0° to 60°.

5. The method for hair dyeing or bleaching according to claim 1, further comprising applying the foam of the mixed solution to a hairline or a parted area of hair.

6. The method for hair dyeing or bleaching according to claim 1, further comprising applying the foam of the mixed solution to a hairline or a parted area of hair with a larger amount than other areas.

7. The method for hair dyeing or bleaching according to claim 1, further comprising rubbing the foam of the mixed solution into hair.

8. The method for hair dyeing or bleaching according to claim 1, wherein pH in the mixed solution is from 8 to 12.

9. The method for hair dyeing or bleaching according to claim 1, wherein the foaming agent is a surfactant.

10. The method for hair dyeing or bleaching according to claim 9, wherein the surfactant is at least one selected from the group consisting of nonionic surfactants, anionic surfactants, cationic surfactants, ampholytic surfactants, and semipolar surfactants.

11. The method for hair dyeing or bleaching according to claim 1, wherein at least one of the first agent or the second agent contains a higher alcohol.

12. The method for hair dyeing or bleaching according to claim 1, wherein the viscosity (25° C.) of the mixed solution is from 3 mPa s to 50 mPa s.

13. The method for hair dyeing or bleaching according to claim 3, wherein the squeezing is carried out while an angle formed between an upright direction of the squeeze container and a vertical direction is in a range of from 5° to 50°.

14. The method for hair dyeing or bleaching according to claim 1, wherein the squeezing is carried out so that both opposing sides of the container body touch each other.

15. The method for hair dyeing or bleaching according to claim 1, wherein a hydrogen peroxide concentration in the second agent is from 1 mass % to 9 mass %.

16. The method for hair dyeing or bleaching according to claim 7, wherein the hair is washed 3 to 60 minutes after rubbing the foam into the hair.

17. The method for hair dyeing or bleaching according to claim 1, further comprising applying the foam of the mixed solution to all the hair.

* * * * *

UNITED STATES PATENT AND TRADEMARK OFFICE
CERTIFICATE OF CORRECTION

PATENT NO. : 10,226,649 B2
APPLICATION NO. : 12/532934
DATED : March 12, 2019
INVENTOR(S) : Hiroyuki Fujinuma et al.

Page 1 of 1

It is certified that error appears in the above-identified patent and that said Letters Patent is hereby corrected as shown below:

In the Claims

Claim 12, Column 16, Line 3:
Please delete "is from 3 mPa s to 50 mPa s".
Please insert -- is from 3 mPa·s to 50 mPa·s --.

Signed and Sealed this
Seventh Day of May, 2019

Andrei Iancu
*Director of the United States Patent and Trademark Office*